United States Patent
Lahme et al.

(10) Patent No.: US 9,744,334 B2
(45) Date of Patent: Aug. 29, 2017

(54) MEDICAL DEVICE FOR INTRODUCING INTO A BODILY ORIFICE OR CAVITY OF AN INDIVIDUAL

(71) Applicants: UROTECH MEDIZINISCHE TECHNOLOGIE GMBH, Rohrdorf-Achenmühle (DE); Sven Lahme, Pforzheim (DE); Wolfhard Pinkowski, Aschheim (DE); Werner Schwarz, Ruhpolding (DE)

(72) Inventors: Sven Lahme, Pforzheim (DE); Wolfhard Pinkowski, Aschheim (DE); Werner Schwarz, Ruhpolding (DE)

(73) Assignee: Urotech GmbH, Rohrdorf-Achenmuehle (DE)

( * ) Notice: Subject to any disclaimer, the term of this patent is extended or adjusted under 35 U.S.C. 154(b) by 122 days.

(21) Appl. No.: 14/437,257

(22) PCT Filed: Oct. 18, 2013

(86) PCT No.: PCT/DE2013/000618
§ 371 (c)(1),
(2) Date: Apr. 21, 2015

(87) PCT Pub. No.: WO2014/063675
PCT Pub. Date: May 1, 2014

(65) Prior Publication Data
US 2015/0265803 A1 Sep. 24, 2015

(30) Foreign Application Priority Data

Oct. 22, 2012 (DE) .................. 10 2012 020 693
May 15, 2013 (DE) .................. 10 2013 008 316

(51) Int. Cl.
*A61M 25/00* (2006.01)
*A61M 29/00* (2006.01)

(52) U.S. Cl.
CPC ........ *A61M 25/0074* (2013.01); *A61M 29/00* (2013.01); *A61M 2025/0004* (2013.01);
(Continued)

(58) Field of Classification Search
CPC .. A61M 2025/0004; A61M 2025/0024; A61M 2210/1078; A61M 2210/1089;
(Continued)

(56) References Cited

U.S. PATENT DOCUMENTS 7,654,989 B2  2/2010  Knapp
8,025,647 B2  9/2011  Siess et al.
(Continued)

FOREIGN PATENT DOCUMENTS

DE   203 04 533 U1   8/2004
EP   1 173 248 B1    10/2011
WO   2011/084342 A1  7/2011

OTHER PUBLICATIONS

International Search Report of PCT/DE2013/000618, mailed Feb. 6, 2014.

*Primary Examiner* — Quynh-Nhu H Vu
(74) *Attorney, Agent, or Firm* — Collard & Roe, P.C.

(57) ABSTRACT

A medical device for inserting into a bodily orifice or cavity of an individual, which includes a first longitudinal hollow body and a second longitudinal hollow body that receives the first hollow body. Between the one end thereof and the first hollow body, there is a stepped transition which extends in the radial direction and can pass into an at least substantially step-free transition by virtue of the fact that the first hollow body, in the region of the stepped transition, expands in the radial direction towards the second hollow body and/or that the second hollow body, in the region of the stepped transition, contracts in the radial direction towards the first hollow body.

8 Claims, 8 Drawing Sheets

(52) U.S. Cl.
CPC .............. *A61M 2025/0024* (2013.01); *A61M 2210/1078* (2013.01); *A61M 2210/1089* (2013.01)

(58) Field of Classification Search
CPC .. A61M 25/0074; A61M 29/00; A61M 25/00; A61M 2025/0175; A61M 2025/0681
See application file for complete search history.

(56) References Cited

U.S. PATENT DOCUMENTS

| | | | |
|---|---|---|---|
| 2005/0010178 A1* | 1/2005 | Katz | A61M 5/3286 604/272 |
| 2005/0240227 A1* | 10/2005 | Bonutti | A61B 17/0401 606/232 |
| 2007/0208276 A1 | 9/2007 | Kornkven Volk et al. | |
| 2011/0152760 A1* | 6/2011 | Parker | A61F 2/95 604/96.01 |
| 2012/0277845 A1* | 11/2012 | Bowe | A61M 25/0068 623/1.11 |

* cited by examiner

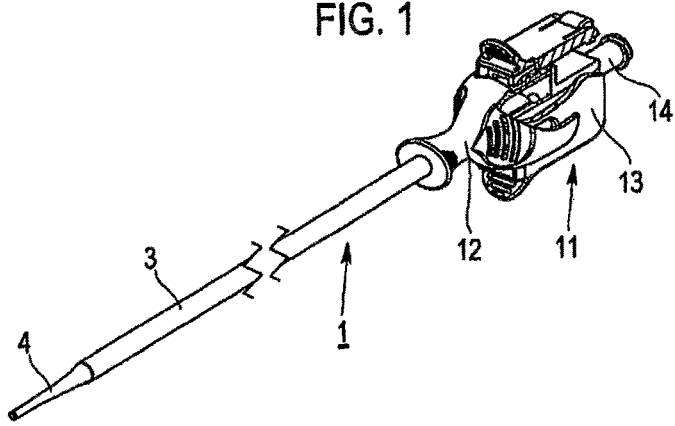
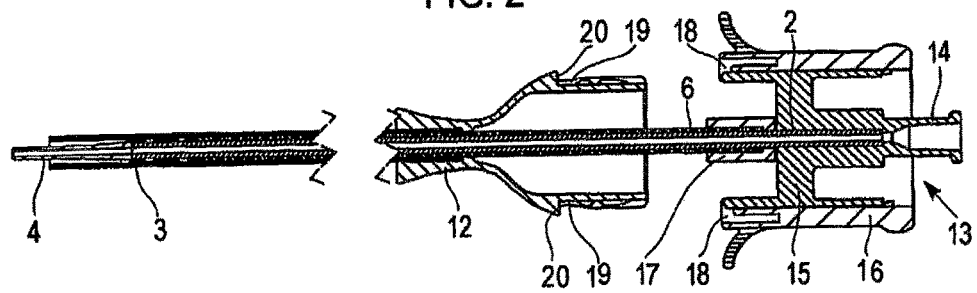
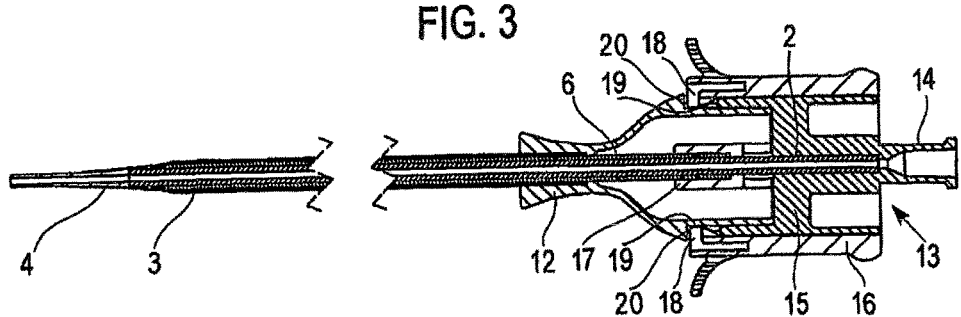

MEDICAL DEVICE FOR INTRODUCING INTO A BODILY ORIFICE OR CAVITY OF AN INDIVIDUAL

CROSS REFERENCE TO RELATED APPLICATIONS

This application is the National Stage of PCT/DE2013/000618 filed on Oct. 18, 2013, which claims priority under 35 U.S.C. §119 of German Application No. 10 2012 020 693.3 filed on Oct. 22, 2012 and German Application No. 10 2013 008 316.8 filed on May 15, 2013, the disclosures of which are incorporated by reference. The international application under PCT article 21(2) was not published in English.

The present invention proceeds from a medical device for introduction into a bodily orifice or cavity of an individual, having a first elongated hollow body and a second elongated hollow body in which the first hollow body is accommodated, wherein a step-shaped transition is present between an end of the second hollow body, from which the first hollow body projects with its distal end, which is intended for introduction into a bodily orifice or cavity of an individual, and this first hollow body, which transition runs in the radial direction.

A device of the aforementioned type is used, for example, as a medical dilator device and, in particular, as what is called a ureter dilator. Such a dilator device has been indicated in U.S. Pat. No. 7,654,989 B2 and EP 1,173,248 B1, for example. In these known dilator devices, however, a step-shaped transition is formed between the outside of a dilator tube and the distal end side of a sheathing tube that accommodates the dilator tube, in each instance. This step-shaped transition is sometimes perceived to be bothersome during use of the dilator device in question, because it can lead to injuries to patients in whom such a device is used.

Sometimes, however, the additional desire exists to also dispense flushing fluid into the bodily orifice or cavity of the individual by the device of the aforementioned type, into which the device in question can be or is introduced, and to drain the flushing fluid from the bodily orifice or cavity in question.

In order to be able to dispense a flushing fluid from a dilator device, it is already known (see, for example, U.S. Pat. No. 7,654,989 B2) to configure the dilator device to have at least two lumens.

The one lumen of the device in question is formed by the passage opening of a guide tube and serves to accommodate the actual dilator. At least one further lumen is situated in an additional tube provided on the outside of the guide tube, and serves to pass a flushing fluid through. With this, however, such a two-lumen dilator device does not have a separate return channel for draining the flushing fluid introduced into a bodily orifice or cavity of an individual. Furthermore, because of the placement of the additional tube on the outside of the guide tube, the outside dimension of the known dilator device is also increased in undesired manner. It is true that it would be possible to integrate the additional tube lumen into the outside circumference of the guide tube lumen. However, as a result the inner lumen of the guide tube would either become smaller, in undesired manner, if the outside dimension of the guide tube remains unchanged, or the outside dimension of the guide tube would also be increased, in undesired manner, if the inner lumen of the guide tube remains unchanged.

The invention is therefore based on the task of showing a way how, proceeding from a medical device of the type stated initially, the step-shaped transition that runs in the radial direction between the one end of the second hollow body, from which the first hollow body projects, and this first hollow body, can be eliminated, at least to the greatest possible extent, in relatively simple manner.

Furthermore, a medical device of the type stated initially is supposed to be developed further in such a manner that it can additionally be used as a flushing device, both for dispensing a flushing fluid into a bodily orifice or cavity of an individual and for draining the flushing fluid from the bodily orifice or cavity in question, without the outside dimension of the device having to be changed in the region of its introduction into the bodily orifice or cavity.

The task indicated above is accomplished, according to the invention, proceeding from a medical device of the type stated initially, for one thing in that the distal end of the first hollow body is configured as a tip part or has a tip part, which runs all the way to the second hollow body, forming the step-shaped transition, that a shaping device that can be displaced in its longitudinal direction is accommodated between the tip part and the second hollow body, and that the shaping device is formed, in the region of the step-shaped transition, in such a manner that by its displacement in the longitudinal direction in question, the tip part can be expanded in the radial direction, toward the step-shaped transition, with cancellation of the latter, to at least a great extent, to form a step-free transition and/or the second hollow body can be contracted in the radial direction, toward the step-shaped transition, with cancellation of the latter, to at least a great extent, to form a step-free transition.

The invention brings with it the advantage that the step-shaped transition that runs in the radial direction between the one end of the second hollow body, from which the first hollow body projects, and this first hollow body can be eliminated, at least to a great extent, in relatively simple manner. The transition, which is at first step-shaped, can therefore be converted into a transition that is step-free, to a great extent, by the present invention, in advantageous manner. However, such a step-free transition is required for problem-free introduction of the device in question into the most varied orifices. When using the device according to the invention as a medical device, such as a ureter dilator, for introduction into a bodily orifice or cavity of an individual, use of the device without the risk of injury is therefore advantageously made possible.

According to a practical further development of the medical device according to the invention, the shaping device has a shaping part that has a pressing part on its outside, in its region to be moved toward the step-shaped transition between the tip part and the second hollow body, by which pressing part the tip part, which has the smaller outside dimension in the radial direction, in the adjacent region between the tip part and the second hollow body, can be expanded all the way to the greater outside dimension, in the radial direction, of the second hollow body. In this way, the advantage of relatively low design effort is obtained, in order to convert the aforementioned step-shaped transition between the tip part and the second hollow body into an at least approximately step-free transition.

According to another practical further development of the medical device according to the invention, the shaping device has a shaping part that has a depression part on its outside, in its region to be moved toward the step-shaped transition between the tip part and the second hollow body, by which depression part the second hollow body, which has the greater outside dimension in the radial direction, in the adjacent region between the tip part and the second hollow body, can be lowered all the way to the tip part, which has the smaller outside dimension in the radial direction. By this practical further development, which can be applied either alternatively or in addition to the practical further development of the medical device according to the invention first indicated, the advantage of relatively low design effort is also obtained, in order to convert the aforementioned step-shaped transition between the tip part and the second hollow body into an at least approximately step-free transition.

Preferably, the shaping part is configured to be hollow in the longitudinal direction of the two hollow bodies. In this way, it is possible to make do with a particularly simple shaping part, which can furthermore be configured to be cylindrical in its longitudinal direction.

Preferably, the two hollow bodies are also configured to be cylindrical. This brings with it the advantage that it is possible to make do with hollow bodies that can be produced in relatively simple manner.

It is practical if a slide mechanism is connected with at least one of the two hollow bodies and the shaping device, by the activation of which mechanism the shaping device can be displaced relative to at least one of the two hollow bodies, in the longitudinal direction of the hollow body. By this measure, the advantage is obtained that it is possible to make do with a relatively low design effort for the longitudinal displacement of the shaping device.

Preferably, the slide mechanism consists of an accommodation part connected with the one hollow body and a contact part connected with the shaping device, which contact part can be laid into or against the accommodation part and can be displaced, relative to the latter, in the longitudinal direction of the hollow bodies. This results in the advantage of an easy to operate slide mechanism, both with regard to joining and with regard to separating accommodation part and contact part.

According to a further practical embodiment of the invention, the slide mechanism has a locking device between the accommodation part and the contact part, which device allows displacement of the shaping body, relative to at least one of the hollow bodies, only after or during the course of locking of the contact part on or in the accommodation part. In this way, the advantage of particularly safe operability of the slide mechanism is achieved, as will still become evident in greater detail below.

Preferably, the medical device according to the invention is configured, in terms of both its basic form and with the inclusion of the embodiments and further developments indicated above, as a medical dilator, at the distal end of which, which serves for introduction into a bodily orifice or cavity of an individual, a dilator tube provided with or connected with a tip part is provided as a first hollow body, which is accommodated by an outer tube as a second hollow body, between which and the dilator tube the shaping device, which can be displaced in the longitudinal direction, is accommodated. This results in the advantage that introduction of the dilator, for example formed by a ureter dilator, into a bodily orifice or cavity of an individual for the purpose of dilation, cannot lead to injuries to the individual in question as a result of this introduction.

The invention will at first be explained below using drawings of a concrete exemplary embodiment of a medical device according to the invention, and then making reference to several possible alternative solutions for converting a step-shaped transition that is present between two hollow elements that border on one another in such a medical device into a step-free transition, at least to a great extent.

The task stated above is accomplished, according to the invention, in a medical device of the type stated initially, for one thing in that the first elongated hollow body and the shaping device can be replaced by an elongated third hollow body having such an outside dimension that an interstice is formed between the outside of the third hollow body and the inside of the first hollow body, and that this interstice can be used, when dispensing a flushing fluid through the third hollow body, into a bodily orifice or cavity of an individual, as a return flow channel for flushing fluid exiting from the bodily orifice or cavity in question, which might be carrying solids with it.

By the reconfiguration of the medical device mentioned initially, as indicated above, the first hollow body and the shaping device are thereby replaced by a third hollow body, which forms a flushing channel for dispensing a flushing fluid into a bodily orifice or cavity of an individual with its interior, and which has such an outside dimension that an interstice is formed between it and the inside dimension of the first hollow body. In this connection, this interstice, when a flushing fluid is dispensed through the third hollow body, forms a return flow channel for flushing fluid exiting from the bodily orifice or cavity in question, which might be carrying solids with it.

The invention brings with it the advantage that the medical device of the type stated initially can be used, in relatively simple manner, not only for introduction into a bodily orifice or cavity of an individual, but also as a flushing device for introduction of a flushing fluid into the bodily orifice of cavity in question, and, at the same time, for draining flushing fluid exiting from this bodily orifice or cavity, which fluid might be carrying solids with it, if necessary by additional suction. With regard to the device of the type stated initially, the outside dimension of this device, in the region of its introduction into the bodily orifice or cavity, is furthermore not changed by the invention; instead, the outside dimension of the device in the region of its introduction into the bodily orifice or cavity remains unchanged.

It is practical if a slide mechanism is connected with at least one of the hollow bodies comprising the second hollow body and the third hollow body, by the activation of which mechanism the third hollow body, after its introduction into the second hollow body, is displaceable in the longitudinal direction of the latter. By this measure, the advantage is obtained that it is possible to make do with a relatively low design effort for the longitudinal displacement of the third hollow body.

According to a further embodiment of the invention, the slide mechanism consists of an accommodation part connected with one of the hollow bodies comprising the second hollow body and the third hollow body, and a contact part connected with the other hollow body, which contact part can be accommodated by the accommodation part and can be displaced, relative to the latter, in the longitudinal direction of the hollow bodies. This results in the advantage of particularly convenient operability of the slide mechanism with regard to both joining and separating accommodation part and contact part.

Preferably, the slide mechanism has a locking device between the accommodation part and the contact part, which device allows displacement of the third hollow body relative to the first hollow body only until the contact part locks onto or into the accommodation part. In this way, the advantage of particularly safe operability of the slide mechanism is achieved, as will become evident in greater detail below.

According to a further embodiment of the invention, the locking device is formed by at least one engagement element in the contact part or in the accommodation part, and by at least one accommodation in the accommodation part or in the contact part. This brings with it the advantage of a relatively simple locking device.

According to a yet further practical embodiment of the invention, the respective accommodation is configured in such a manner that the engagement element accommodated by it can preferably be displaced transverse to the longitudinal direction of the device, in the related accommodation, after accommodation part and contact part have been locked. This measure is of very particular advantage, in order to bring the third hollow body accommodated by the second hollow body to the inside of the second hollow body with its outside and to thereby increase the interstice between a region of its outside and the inside of the second hollow body that lies opposite to it on one side. This can be beneficial in the case that the flushing fluid exiting from a bodily orifice or cavity of an individual, which fluid had been introduced into this bodily orifice or cavity through the third hollow body, carries larger solids with it to be drained away, which could not be drained away with a concentric arrangement of the third hollow body in the second hollow body, through the concentric interstice that would then be present.

Also, the task underlying the invention is accomplished, according to the invention, in the case of a medical device of the type stated initially, in that when the tip part is formed by a rigid tip part provided at the distal device end and a radially expandable transition part that follows it, toward the proximal device end, which transition part can be expanded, by displacement of the shaping device from a first position, in which the part forms a step-shaped transition with the second hollow body, to a second position in which the part forms the step-free transition with the second hollow body, and when an interstice is present between the outside of the shaping device and the inside of the second hollow body, the interior of the shaping device, after removal of the first hollow body including its tip part, with exposure of the said interstice toward the distal device end, can be used as a flushing channel for dispensing a flushing fluid into a bodily orifice or cavity of an individual, and the said interstice can be used as a return flow channel for flushing fluid exiting from the bodily orifice or cavity in question, which might be carrying solids with it.

By this reconfiguration of the medical device stated initially, as just indicated, the interior of the shaping device thereby forms a flushing channel for dispensing a flushing fluid into a bodily orifice or cavity of an individual, after removal of the first hollow body including its tip part, with exposure of the said interstice toward the distal device end. The said interstice forms a return flow channel for flushing fluid exiting from the bodily orifice or cavity in question, which might be carrying solids with it.

This, too, results in the advantage that the medical device of the type stated initially can be used in relatively simple manner not only for introduction into a bodily orifice or cavity of an individual, but also as a flushing device for introduction of a flushing fluid into the bodily orifice or cavity in question, and, at the same time, for draining the flushing fluid exiting from this bodily orifice or cavity, which might be carrying solids with it, if necessary by additional suction. With regard to the device of the type stated initially, the outside dimension of this device, in the region of its introduction into the bodily orifice or cavity, is furthermore not changed by the solution for the task underlying the invention as just indicated; instead, the outside dimension of the device in the region of its introduction into the bodily orifice or cavity remains unchanged.

It is practical in the configuration of the medical device stated initially, as just indicated, that the first hollow body is releasably held in place on the proximal device end by a locking mechanism. This brings with it the advantage not only of particularly simple securing of the first hollow body and of the tip part held by it in the second hollow body, but also of simple release of the first hollow body and of the tip part held by it from the second hollow body.

Preferably, the locking mechanism mentioned above is contained in a contact part that can be accommodated by an accommodation part that carries the second hollow body. In this way, the locking mechanism can be implemented in advantageous manner, with particularly low design effort.

Furthermore, the task underlying the invention is accomplished, according to the invention, in the case of a medical device of the type stated initially, in that when the tip part is formed by a rigid tip part provided at the distal device end and a radially expandable transition part that follows it, toward the proximal device end, which transition part can be expanded, by displacement of the shaping device from a first position, in which the part forms the step-shaped transition with the second hollow body, to a second position in which the part forms the step-free transition with the second hollow body, and when an interstice is present between the outside of the tube part and the inside of the second hollow body, the interior of the first hollow body, after removal of the tip part alone, with exposure of the said interstice toward the distal device end, can be used as a flushing channel for dispensing a flushing fluid into a bodily orifice or cavity of an individual, and the said interstice can be used as a return flow channel for flushing fluid exiting from the bodily orifice or cavity in question, which might be carrying solids with it.

By this reconfiguration of the medical device stated initially, as just indicated, the interior of the first hollow body thereby forms a flushing channel for dispensing a flushing fluid into a bodily orifice or cavity of an individual, after removal of the tip part alone, with exposure of the said interstice toward the distal device end, and the said interstice forms a return flow channel for flushing fluid exiting from the bodily orifice or cavity in question, which might be carrying solids with it.

This reconfiguration of the medical device stated initially also results in the advantage that this medical device can be used in relatively simple manner not only for introduction into a bodily orifice or cavity of an individual, but also as a flushing device for introduction of a flushing fluid into the bodily orifice or cavity in question, and, at the same time, for draining the flushing fluid exiting from this bodily orifice or cavity, which might be carrying solids with it, if necessary by additional suction. With regard to the device of the type stated initially, the outside dimension of this device, in the region of its introduction into the bodily orifice or cavity, is furthermore not changed by the solution for the task underlying the invention as just indicated; instead, the outside dimension of the device in the region of its introduction into the bodily orifice or cavity remains unchanged.

Preferably, in the configuration of the medical device stated initially, as just indicated, the tip part is connected with the first hollow body by a releasable connection device. This results in the advantage of a particularly simple possibility of separating the tip part from the first hollow body.

Preferably, the releasable connection device mentioned above is formed by a screw connection. As a result, a simple and, at the same time, secure connection device is available for connecting tip part and first hollow body, in advantageous manner, which device allows easy separation of the tip part from the first hollow body.

FIG. 1 shows, in a perspective representation, not to scale, an exemplary embodiment of a medical device according to the invention, in the form of a ureter dilator.

FIG. 2 shows, in a sectional view, not to scale, the medical device according to the invention shown in FIG. 1, in the non-assembled state.

FIG. 3 shows, in a sectional view, not to scale, the medical device according to the invention shown in FIG. 2, in the assembled state.

Before the drawings are discussed in any detail, it should first be noted that corresponding parts or elements in all of the drawing figures are referred to with the same reference symbols.

Figure 4:
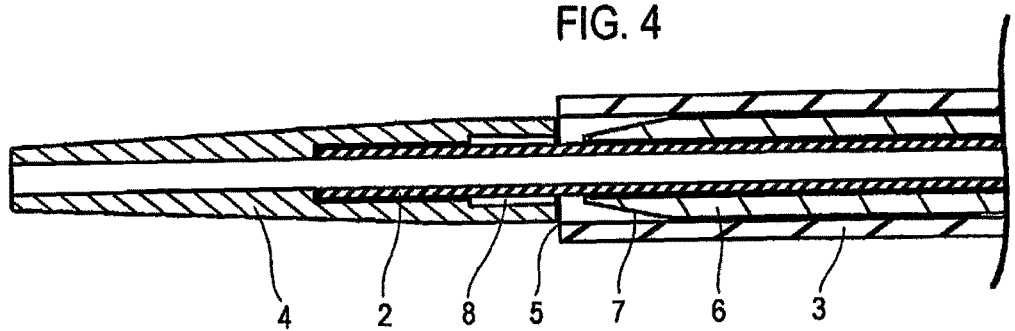
FIG. 4 shows, in a greatly magnified sectional view, the distal region of the medical device shown in FIG. 1 to 3, intended for introduction into a bodily orifice or cavity of an individual, in a state in which a step-shaped transition exists between two adjacent hollow elements.

In FIG. 1 to 5, a medical device 1 according to the invention, in the form of a dilator 1, is shown as an exemplary embodiment of the invention, in a perspective representation, not to scale.

This dilator 1, which can particularly be a ureter dilator, serves for introduction into a bodily orifice or cavity of an individual (not shown), and has a first elongated hollow body 2 and a second elongated hollow body 3, in which the first hollow body 2 is accommodated, shown in greater detail in FIG. 2 to 5.

The two hollow bodies 2 and 3 of the dilator 1 are configured to be cylindrical here, in other words are each formed by a tube. The first hollow body 2, which forms a dilator tube 2, is configured as a tip part 4 at its distal end—this is the end shown at the left in FIG. 1—or has such a separate tip part 4, as is evident in greater detail in FIG. 2 to 5. This tip part 4, which is configured in the shape of a cone or truncated cone on its outer longitudinal side, runs all the way to the second hollow body 3, which represents an outer tube, forming the step-shaped transition 5 that has already been mentioned (see FIG. 4). The tip part 4 is thereby part of the first hollow body 2, to an extent, which body—to say it differently—consists of an elongated cylindrical part and the tip part 4.

At first, a step-shaped transition 5 that runs in the radial direction is formed between the distal end of the second hollow body 3, from which the first hollow body 2 projects with its tip part 4 that serves for introduction into a bodily orifice or cavity of an individual, and this tip part 4, as is evident from the greatly magnified sectional view of FIG. 4.

At this point, it should be noted that the outer hollow body 3 of the dilator 1 will have a diameter of about 2 mm to 6 mm and a length of about 5 cm to 100 cm in the case that it is structured as a cylindrical tube, in its actual embodiment.

Figure 5:
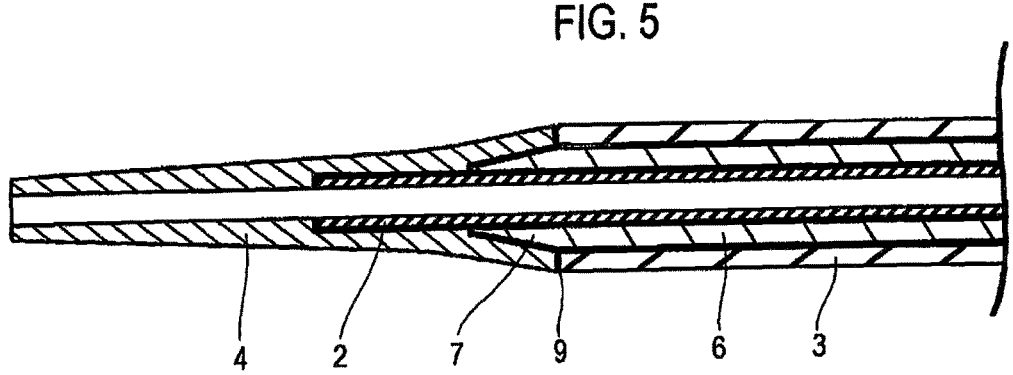
FIG. 5 shows, in a greatly magnified sectional view, the distal region of the medical device shown in FIG. 1 to 3, intended for introduction into a bodily orifice or cavity of an individual, in a state in which the step-shaped transition between two adjacent hollow elements shown in FIG. 4 has been converted into a transition that is step-free, at least to a great extent.

As is evident from FIG. 2 to 5, a shaping device that is displaceable in the longitudinal direction of the body/tube is accommodated between the tip part 4 and the second hollow body 3 or outer tube 3, which device consists, according to FIGS. 4 and 5, of a shaping part 6 and a pressing part 7. The shaping part 6 and the pressing part 7 can be formed, as in the present case, cohesively by a single cylindrical part having a tip in the form of a conical stump that acts as a pressing element.

As is evident in greater detail from FIGS. 4 and 5, the pressing part 7 of the shaping device is formed, in the region of the step-shaped transition 5, in such a manner that the tip part 4 can be expanded, at the step-shaped transition, in the radial direction, by displacement of the part in the longitudinal direction in question, to form a step-free transition 9, canceling out this step-shaped transition 5, at least to a great extent. The pressing part 7, which is configured in the shape of a cone or truncated cone here, is pushed into an accommodation space 8 of the tip part 4 during the course of its aforementioned longitudinal displacement, which space is filled by the pressing part 7, at least to a great extent, after the longitudinal displacement has taken place. As is evident from FIG. 2 to 5, in the present dilator 1 the shaping part 6 and the pressing part 7 are hollow, in each instance, and particularly configured to be cylindrical. In this connection, the tip part 4 will consist, at least in the region of the aforementioned step-shaped transition 5, as will the outer tube 3 and the shaping device 6, 7, of a hose material such as a tough-elastic plastic hose; in the case of the tip part 4, this plastic hose can be expanded in its radial direction by the pressing part 7 of the shaping device, and after this part is retracted, it can contract or narrow again in its radial direction. The materials to be used for the medical device 1 must, of course, be biocompatible, to the extent that they come into contact with tissue of a bodily orifice or cavity of an individual, into which the device in question is introduced.

In order to facilitate the expansion of the tip part 4 mentioned above, this part can be slit in its longitudinal direction, preferably by several, for example four slits in its region adjacent to the aforementioned step-shaped transition. This slitting can have a length in the range of 2 to 20 mm, for example, in an actual embodiment.

However, at this point it should be noted that alternatively or in addition to the embodiment considered above, the shaping device can also be shaped, in the region of the step-shaped transition 5, in such a manner that the outer tube 3 that forms the second hollow body 3 can be narrowed or contracted at the step-shaped transition, in the radial direction, to form a step-free transition, with cancellation of the step-shaped transition, at least to a great extent. This will be discussed in greater detail below, making reference to FIG. 8 to 11. In this connection, in such a case the outer tube 3 in question will consist of a hose material, such as a tough-elastic plastic hose, at least in the region of the aforementioned step-shaped transition 5, which hose can be expanded by the shaping device, in its radial direction, and which contracts or narrows again in its radial direction, after the device has been removed.

Before further details in FIG. 1 to 3 are discussed, alternative solutions shown in FIG. 6 to 11 for converting the step-shaped transition 5 into a step-free transition 9 will first be considered. In the case of these alternative solutions, as well, it is assumed that the shaping device as well as the respective outer tube 3 and/or the tip part 4 consist of a hose material, such as a tough-elastic plastic hose material. In the case of the outer tube 3 and/or of the tip part 4, this plastic hose can be expanded in its radial direction, by the shaping device, at least in the region of the aforementioned step-shaped transition 5, and it can contract or narrow in its radial direction again after the device has been retracted.

In general, the second hollow body or outer tube 3 and/or the shaping device can consist of a hollow, elastic longitudinal spiral produced from a metal or plastic, in each embodiment of the device according to the invention. By such flexible longitudinal spirals, the device according to the invention can be introduced relatively conveniently into bodily orifices that run in different directions, to the progressions of which the longitudinal spirals can easily adapt. After retraction of the device in question from such bodily orifices, the longitudinal spirals can they easily resume their starting shapes, which can be stretched-out shapes, for example.

Figure 6:
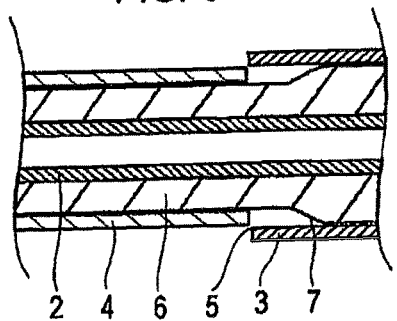
FIGS. 6 and 7 show an alternative solution to the solution shown in FIGS. 4 and 5 for converting a step-shaped transition between two adjacent hollow elements into a transition that is step-free, at least to a great extent.
Figure 7:
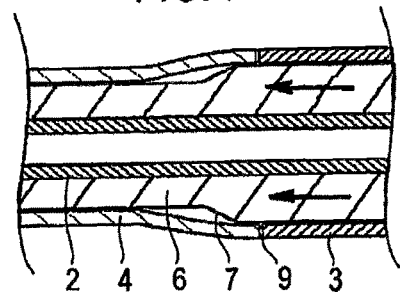

FIGS. 6 and 7 show a first alternative solution for converting the aforementioned step-shaped transition 5 into a step-free transition 9, at least to a great extent. In this connection, merely the region around the transition in question is shown on a greatly magnified scale. FIG. 6 shows the state before longitudinal displacement of the shaping part 6 with its pressing part 7, and FIG. 7 shows the state after the longitudinal displacement has taken place in the direction of the arrows indicated there. Therefore corresponding expansion of the tip part 4 takes place here in the region of the step-shaped transition 5, as in the embodiment shown in FIG. 2 to 5.

Figure 8:
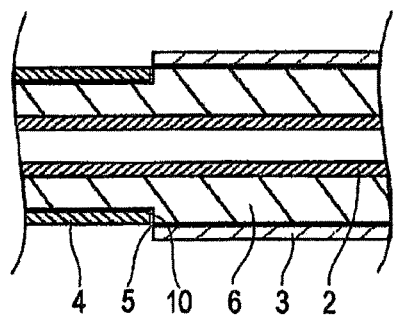
FIGS. 8 and 9 show a further alternative solution to the solution shown in FIGS. 4 and 5 for converting a step-shaped transition between two adjacent hollow elements into a transition that is step-free, at least to a great extent.
Figure 9:
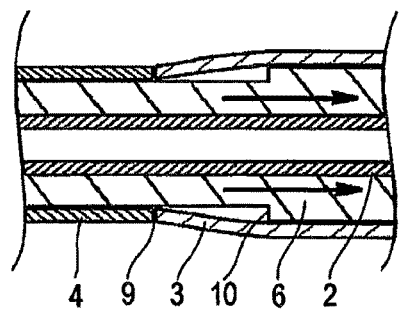

In FIGS. 8 and 9, a further alternative solution for converting the aforementioned step-shaped transition 5 into a step-free transition 9, at least to a great extent, is shown. In this connection, here, too, merely the region around the transition in question is shown on a greatly magnified scale. In contrast to the alternative solution described above, the shaping device has a depression part 10 on the shaping part 6, in the form of a step, according to FIGS. 8 and 9. This depression part 10 releases the support of the outer tube in the radial direction when the shaping part 6 is longitudinally displaced in the direction of the arrows indicated in FIG. 9, and the outer tube can then contract in the radial direction and forms the step-free transition 9 with the tip part 4.

Figure 10:
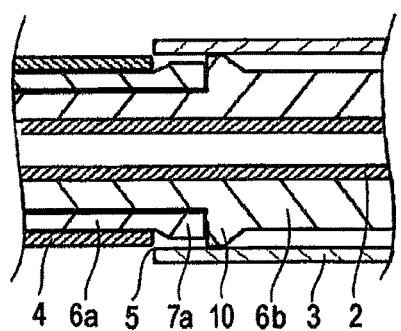
FIGS. 10 and 11 show yet another alternative solution to the solution shown in FIGS. 4 and 5 for converting a step-shaped transition between two adjacent hollow elements into a transition that is step-free, at least to a great extent.
Figure 11:
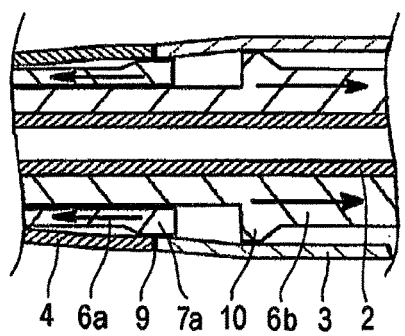

In FIGS. 10 and 11, yet a further alternative solution for converting the aforementioned step-shaped transition 5 into a step-free transition 9, at least to a great extent, is shown. While in the designs considered above for converting the aforementioned step-shaped transition 5 into a step-free transition 9, at least to a great extent, the shaping part 6 of the shaping device can be displaced only in a longitudinal direction, in each instance, FIGS. 10 and 11 show a device in which the shaping device comprises not only a shaping part 6a having a pressing part 7a but also a shaping part 6b having a depression part 10. To convert the step-shaped transition 5 that is at first present between the outer tube 3 and the tip part 4 into an at least approximately step-free transition 9, the two shaping parts 6a and 6b are displaced in the longitudinal direction from the position shown in FIG. 10, in opposite directions, away from one another, as the arrows entered in FIG. 11 show. It is practical if this displacement takes place simultaneously.

In order to undertake the aforementioned longitudinal displacement of the respective forming device and, in particular, of the respective forming part 6 or 6a, 6b, a slide mechanism 11 is provided, according to the invention, the possible embodiment of which is shown in FIG. 1 to 3. This slide mechanism, partly shown in section in FIG. 1, consists of an accommodation part 12 and a contact part 13 in the present embodiment.

The accommodation part 12 is firmly connected with one of the two hollow bodies 2 and 3, specifically, in the present case, with the outer tube 3 that forms the second hollow body 3. The contact part 13, which can be brought into contact on the accommodation part 12 in the axial direction of the device 1, from its proximal side, which is shown on the right in FIG. 1 to 3, and can be released from the accommodation part 12 in question again, if necessary, consists of an inner part 15 and an outer part 16, in which the inner part 15 is accommodated so as to slide in the axial direction of the device 1. The inner part 15 is firmly connected with the dilator tube 2 that forms the first hollow body 2. At its proximal end, shown on the right in FIG. 1 to 3, the inner part 15 is provided with a connection part 14, to which different medical devices, such as syringes, for example, can be connected. The connection part in question can be, for example, what is called a Luer connection part.

The aforementioned outer part 16 is firmly connected with the proximal end of the shaping part 6 formed by a cylindrical tube, by a sliding part 17 that accommodates the dilator tube 2 so as to slide. This sliding part 17, which has the same crosshatching as the outer part 16, is coherently connected with the outer part 16 by way of a crosspiece, not visible in FIGS. 2 and 3. In this connection, the crosspiece in question runs perpendicular to the drawing plane of FIGS. 2 and 3. Therefore the slide mechanism 11 is connected with the one of the two hollow bodies 2, 3 and the shaping device or with its shaping part 6 or 6a, 6b, by the activation of which mechanism the shaping device can be displaced relative to at least one of the two hollow bodies 2, 3, in the longitudinal direction of the body.

The slide mechanism 11 has a locking device between the accommodation part 12 and the contact part 13, which device is formed, in the present case, by engagement projections 18 on the inside of the outer part 16 of the contact part 13 and engagement projection accommodations 19 that match these engagement projections 18 on the outer circumference of the accommodation part 12. The accommodation part furthermore has stops 20 in the form of projections, which delimit displacement of the entire contact part 13 on the accommodation part 12 in the longitudinal direction of the device. By this locking device, the shaping device with its respective shaping part 6 or 6a and 6b can be displaced relative to the one hollow body only after or during the course of locking of the contact part 13 on or in the accommodation part 12.

In order to be able to perform the longitudinal displacement of the shaping device in the embodiment shown in FIG. 1 to 3, there the inner tube or dilator tube 2 that forms the first hollow body is pushed, together with the shaping device, preferably from the proximal device side, through the outer tube 3 that forms the second hollow body. Removal of the dilator tube 2 from the device 1 takes place by pulling it out of the outer tube 3 toward the proximal device side.

It should be noted at this point that the locking device mentioned above can also be implemented by other locking elements formed on the accommodation part 12 and the contact part 13. The displacement of the contact part 13, making contact with the accommodation part 12, can also be limited in a different way other than the stops 20 present in the form of projections here. For example, the displacement in question can be limited, either in addition to or alternatively to the limitation explained, by contact of the contact part 13 on a different circumference region of the accommodation part 12.

Above, a medical dilator 1 has been explained using an embodiment of the invention, as well as with reference to some alternative solutions. For the dilator tube 2 contained in the dilator 1, with its tip part 4, the outer tube 3 more or less represents a dilator sheath, within which the dilator tube and the shaping device with its shaping part 6 or shaping parts 6a, 6b and with its pressing part 7 or depression part 10 can be displaced.

In the embodiment explained and also in the alternative solutions considered, it has been assumed that the step-shaped transition 5 to be converted into a step-free transition 9 is formed by a region of a tip part 4 having a smaller dimension, in the radial direction, and a second hollow body 3 adjacent to the tip part 4, having a comparatively greater dimension in the radial direction. The step-shaped transition 5 in question therefore represents an expansion of the outside diameter of the device 1 in its radial direction, seen from the distal device end. The present invention, however, is not limited to conversion of such a step-shaped transition 5 into a step-free transition 9. For example, the step-shaped transition in question could also be formed by a region of the tip part 4 that has a greater dimension, in the radial direction, and the second hollow body 3 adjacent to the tip part 4 having a comparatively smaller dimension, in the radial direction. In this case, the respective forming device would have to be turned, with reference to its position, by 180°, in each instance, with reference to the position shown in the drawing figures.

Figure 12:
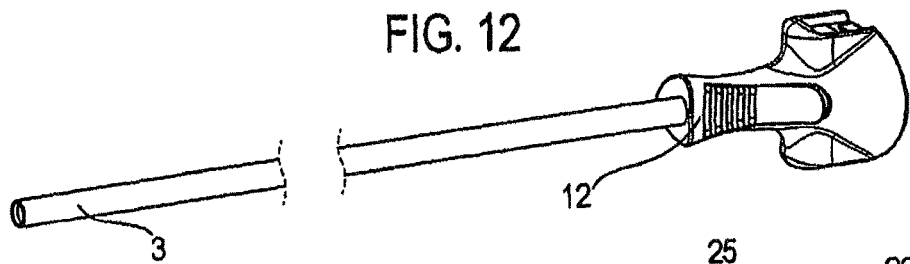
FIG. 12 shows, in a perspective representation, not to scale, the second elongated hollow body of the medical device according to the invention, after its first elongated hollow body and the shaping device have been removed from this second hollow body.

FIG. 12 shows only the outer second elongated hollow body 3 connected with the accommodation part 12 of the slide mechanism 11 shown in FIG. 1, at its proximal end, shown on the right, which part expands toward the proximal end, in funnel shape, of the medical device according to FIG. 1. According to FIG. 12, the first hollow body with its tip part (referred to as 2 or 4 in FIGS. 2 and 3) and the shaping device (referred to as 6 in FIG. 4 to 11) provided in FIG. 1 have therefore been removed from the second hollow body 3 of the medical device according to FIG. 1. Here, too, the second hollow body 3 is formed by a tube having a continuous lumen in its longitudinal direction or by a hose, preferably composed of a biocompatible plastic, such as polyurethane, for example.

The accommodation part 12 is expanded in funnel shape toward its proximal end, in order to accommodate a contact part 13—as will still become evident in greater detail below.

This contact part 13, together with the accommodation part 12, forms the aforementioned slide mechanism 11.

Figure 13:
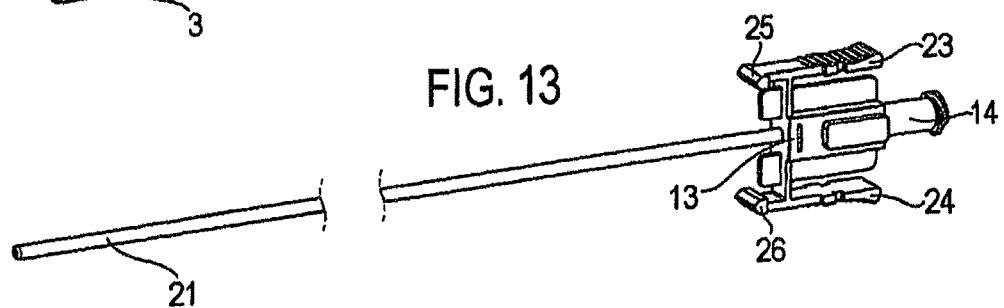
FIG. 13 shows, in a perspective representation, not to scale, a third elongated hollow body, which, in a first further development of the medical device according to the invention, is to be introduced into the second hollow body of the medical device shown in FIG. 1, forming a flushing device.

In FIG. 13, a further elongated hollow body is shown, which is referred to as a third hollow body 21 with reference to the medical device according to FIG. 1 to 3, and through which a flushing fluid can be conducted. This third hollow body 21 is also formed by a tube having a continuous lumen 29 in its longitudinal direction or by a hose, preferably also composed of a biocompatible plastic, such as polyurethane, for example. As will still become evident, the aforementioned lumen 29 in the interior of the third hollow body 21 establishes a flushing channel of the medical device for dispensing a flushing fluid into a bodily orifice or cavity of an individual, into which the device in question has been introduced.

The outside dimension of the third hollow body 21 is smaller, at a right angle to its longitudinal direction, than the inside dimension of the second hollow body 2 at a right angle to its longitudinal direction. In the case that the two hollow bodies 3 and 21 are formed by tubes or hoses, the ratio of the outside diameter of the third hollow body 21 to the inside diameter of the second hollow body 3 can preferably lie between 1:4 and 1:2. As a result, an interstice 22 is formed between the outside of the third hollow body 21 and the inside of the second hollow body 3, as is evident in greater detail from FIG. 15. This interstice 22, as will still become evident in greater detail below, can be used, when a flushing fluid is dispensed through the third hollow body 21 into a bodily orifice or cavity of an individual, as a return flow channel for flushing fluid exiting from the bodily orifice or cavity in question, which might be carrying solids with it, if necessary with the aid of an additional suction device.

At its proximal end, shown on the right in FIG. 13, the third hollow body 21 is connected with the contact part 13 of the slide mechanism 11, which has already been mentioned. The contact part 13 is configured as a flat body that has rocker-like elastic activation elements 23, 24 on its outer narrow sides, which elements have engagement elements 25 and 26, respectively, toward the distal end, which lies on the left in FIG. 13. These engagement elements 25 and 26 can be raised from their position shown in FIG. 13 by exerting pressure on the activation elements 23, 24, in order to then lock the engagement elements 25, 26 into matching accommodations 27 or 28 of the accommodation part 12, or to release such locking again. These accommodations 27 and 28 are evident in greater detail from FIG. 15.

The slide mechanism 11 formed by the accommodation part 12 and the contact part 13 therefore has a locking device that allows displacement of the third hollow body 21 relative to the second hollow body 3 only until the contact part 13 locks onto or into the accommodation part 12.

The contact part 13, as in the medical device according to FIG. 1 to 3, has a connection part 14 at its proximal end, which part has a longitudinal passage, and can preferably be a Luer lock connection part. The longitudinal passage of this connection part 14 is connected with the continuous lumen of the third hollow body 21.

Figure 14:
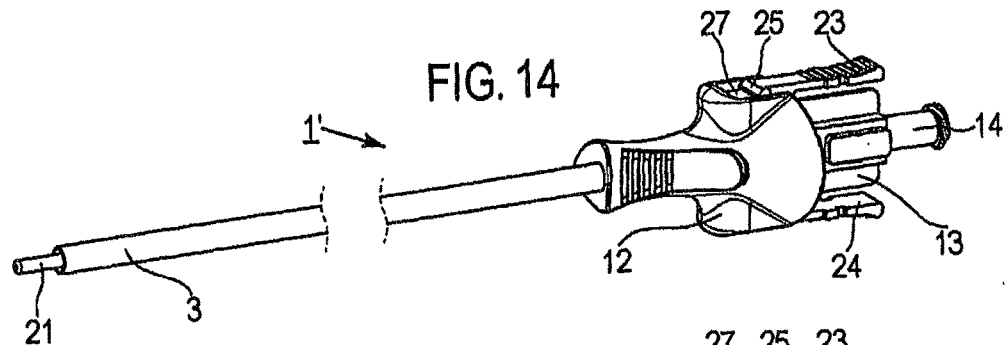
FIG. 14 shows, in a perspective representation, not to scale, the medical device with the third hollow body according to FIG. 13 inserted into the second hollow body according to FIG. 13.
Figure 15:
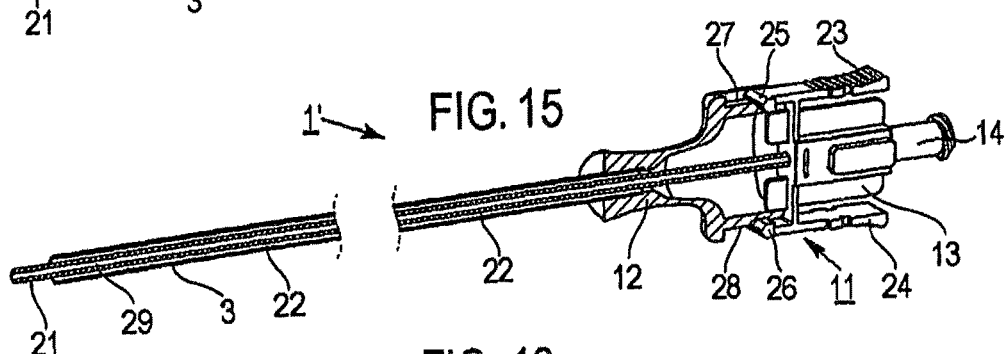
FIG. 15 shows a perspective sectional view of the medical device shown in FIG. 14.

In FIGS. 14 and 15, the outer second hollow body 3 represented in FIG. 12, with the accommodation part 12 that is open in funnel shape toward the proximal end, and the third hollow body 21 represented in FIG. 13 are represented as an inner hollow body with the contact part 13, in the assembled state, as a medical device 1' that is modified, as compared with the medical device according to FIG. 1 to 3, to be a flushing device according to a first embodiment. In this state, the contact part 13 is locked into the accommodation part 12 with regard to longitudinal displaceability, as is clearly evident from the perspective sectional view according to FIG. 15. As a result, the third hollow body 21 is fixed in place within the second hollow body 3 with regard to its longitudinal displaceability. In this connection, the third hollow body 21 projects out of the distal end of the second hollow body 3 by a certain distance with its distal end. In practice, this distance can lie between 1 cm and 10 cm, for example. In this state, a flushing fluid can be introduced into a bodily orifice or cavity of an individual through the third hollow body 21, into which the medical device according to FIG. 1 to 3 has previously been introduced, and the first hollow body of which has been replaced by or exchanged for the third hollow body 21. The interstice 22, formed between the outside of the third hollow body 21 and the inside of the first hollow body 3, can then be used as a return flow channel for the flushing fluid exiting from the bodily orifice or cavity in question, which might be carrying solids with it.

The interstice 22 that serves as a return channel leads into the interior of the contact part 12, as is evident from FIG. 15.

The flushing fluid guided back through this return channel, which might be carrying solids with it, can then flow out to the outside from the proximal end region of the flushing device 1'. This outflow can take place, for example, through the non-sealing contact region between the accommodation part 12 and the contact part 13 and/or by special outflow openings in the accommodation part 12 and/or in the contact part 13. This method of outflow of the flushing fluid, which might be carrying solids with it, out of the return flow channel, can furthermore be applied in corresponding manner in other embodiments of the invention, as well, particularly in the two further embodiments of the invention that will still be described in greater detail below.

Figure 16:
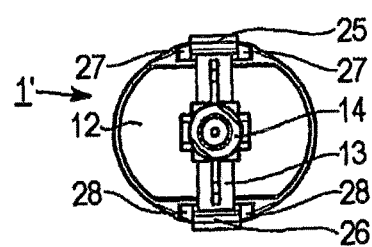
FIG. 16 shows a top view of the proximal end of the medical device shown on the right in FIG. 14.

In FIG. 16, the proximal end of the medical device, shown on the right in FIG. 14, is shown in a top view. In this connection, it is evident that the accommodations 27 and 28 in the accommodation part 12 are wider than the engagement elements 25 and 26 of the contact part 13. As a result, the contact part 13 can be displaced transverse to its longitudinal direction, relative to the accommodation part 12. This displaceability preferably exists only after accommodation part 12 and contact part 13 have been locked together. Fundamentally, the displaceability in question, between accommodation part 12 and contact part 13, can also exist before they have been locked together. By the displacement in question, the third hollow body 21, accommodated by the second hollow body 3, can be brought up to or laid against the inside of the second hollow body 3 with its outside, in order to increase the size of the interstice between its outside and the inside of the second hollow body 3 on one side. This can be of particular benefit in the case that the flushing fluid exiting from a bodily orifice or cavity of an individual, which fluid was previously introduced into the orifice or cavity through the third hollow body 21, brings with it larger solids to be carried away, which could not be carried away in the case of a concentric arrangement of the third hollow body 21 in the second hollow body 3.

Supplementary, in this connection it should still be noted that in deviation from the structure of the locking device formed on the accommodation part 12 and the contact part 13, as explained above, the positions of their engagement elements 25, 26 and their accommodations 27, 28 can also be interchanged.

With the medical device 1' described above, a method for flushing a bodily orifice or cavity, such as a kidney of an individual, by a flushing fluid introduced into the bodily orifice or cavity in question, through the third hollow body 21, is made possible. The flushing fluid that exits from this bodily orifice or cavity again, which fluid might be carrying solids with it, is carried away through the interstice 22 between the outside of the third hollow body 21 and the inside of the second hollow body 3, if necessary by suction. The present medical device is particularly used as a flushing device 1' after the medical device described using FIG. 1 to 3 has been introduced into the aforementioned bodily orifice or cavity, and its first hollow body and the second device in the second hollow body 3 have been replaced with the third hollow body 21 described here. The medical device 1' according to the present invention is therefore formed in that in the medical device according to FIG. 1 to 3, its first elongated hollow body (2 in FIGS. 2 and 3) and the shaping device (6 in FIG. 4 to 11) are exchanged or replaced with the third hollow body 21 described here, depending on whether the medical device according to FIG. 1 to 3 has already been introduced into a bodily orifice or cavity of an individual or is still to be introduced.

Fundamentally, the method for flushing a bodily orifice or cavity, such as a kidney of an individual, as mentioned above can also be carried out solely by the medical device 1' described, without this device previously being configured as a medical device 1 according to FIG. 1 to 3. This means that the medical device 1' can innately also be used alone, in other words without the additional elements 2, 4, and 6 provided in the medical device 1.

Figure 19:
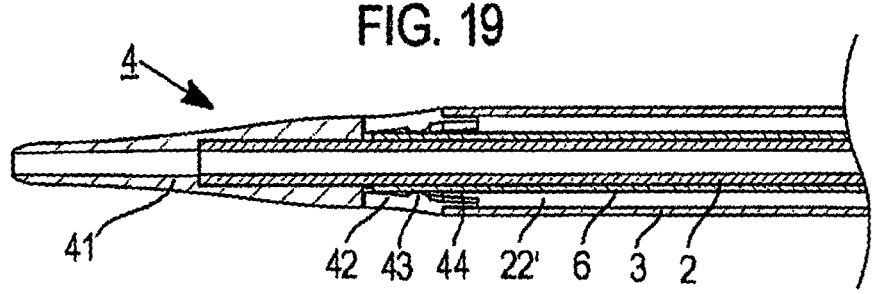
FIG. 19 shows, in a sectional view, not to scale, the embodiment of the distal end region of the medical device shown in FIG. 17, wherein the shaping device is situated in a second adjustment position, different from the first adjustment position.
Figure 20:
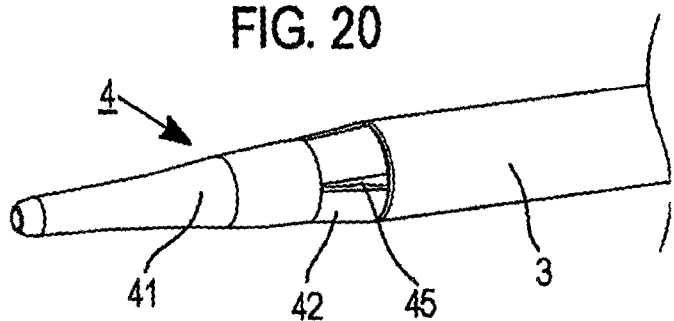
FIG. 20 shows the distal end region of the medical device shown in FIG. 19, in a perspective representation, not to scale.
Figure 21:
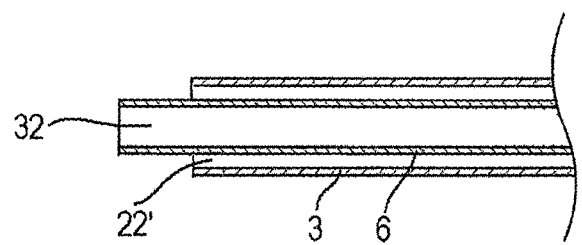
FIG. 21 shows, in a sectional view, not to scale, the distal end region of the medical device shown in FIG. 17 to 20, after reconfiguration of the device in question to form a flushing device according to the present invention.

In FIG. 17 to 20, a further variant of the distal end region of the medical device according to FIG. 1 to 3 is shown, where this modified device with its distal end region can be reconfigured in relatively simple manner, to form a flushing device according to a second embodiment, as is evident from FIG. 21.

According to FIG. 17 to 20, the tip part 4, connected with (for example glued to) the inner first hollow body 2 consists of a rigid tip part 41 and a radially expandable transition part 42 that follows it toward the proximal device end. This transition part 42 can be expanded, by displacement of the shaping device 6 from a first position, in which it forms the step-shaped transition 5 with the second hollow body 3 (shown in FIGS. 17 and 18), to a second position, in which it forms the step-free transition with the second hollow body 3 (shown in FIGS. 19 and 20). The tip part 41 and the transition part 42 are connected with one another at their regions that border on one another, for example by a glued connection.

The transition part 42 is a part that can be expanded in funnel shape from the tip part 41, having a nub region 43 that lies on the inside, by which region such expansion can be brought about when it makes contact with the shaping device 6 (compare FIGS. 17, 18 with FIGS. 19, 20), so that the step-shaped transition 5 (see FIGS. 17 and 18) that is at first present between the proximal end of the transition part 42 and the outer second hollow body 3 can be converted to the step-free transition, at least to a great extent (see FIGS. 19 and 20). At its end facing the proximal device end (that is the end shown on the right, in each instance, in FIG. 17 to 20), the transition part 42 has one or more contact parts 44, with which it lies against the inner wall of the second hollow body 3 as it expands. From this contact part or these contact parts 44, an outer edge region rises from the contact part 44, the height of which region, at a right angle to the longitudinal device direction and thereby at a right angle to the longitudinal direction of the second hollow body 3, is at least approximately equal to its wall thickness. The contact part 44 serves three different purposes. For one thing, it serves to prevent the tip part 4 from hooking into the distal end of the hollow body 3 when the hollow body 2 is retracted (in the case that this hollow body is a dilator) into the hollow body 3 (which serves as a sheath).

Secondly, the contact part 44 limits expansion of the tip part 4, among other things, and thirdly the contact part 44 centers the tip part in the third hollow body 21, which is preferably configured as a tube.

One or more slits 45 can be contained in the circumference region of the transition part 42, in order to facilitate expansion of the transition part 42. These slits 45 furthermore do not need to be continuous openings between the material regions of the transition part 42 that border on one another at them. Instead, the slits 45 in question can be formed by thinned areas of material in the material that forms the transition part 42, between the material regions that border on one another at them.

In the present case, the shaping device 6 is formed by an elongated tube or a hose having an inner lumen 32 and an outside dimension in the radial direction that is smaller than the inside dimension or the inside diameter of the second hollow body 3. The lumen 32 can be used as a flushing channel for dispensing a flushing fluid into a bodily orifice or cavity of an individual, into which the medical device according to the main patent has been introduced with the second hollow body. An interstice 22' is formed between the aforementioned outside dimension of the shaping device 6 and the inside of the second hollow body 3. This interstice 22' can be used as a return flow channel for a flushing fluid, which serves as a flushing channel for dispensing a flushing fluid into a bodily orifice or cavity of an individual after removal of the first hollow body 2 including its tip end 4, with exposure of the interstice 22' toward the distal device end.

This configuration of the medical device last mentioned, as a flushing device, is illustrated in FIG. 21. There, only the shaping device 6 as an inner hollow body element with the lumen 32 as a flushing channel and the second hollow body 3 can be seen at the distal device end, after removal of the first hollow body 2 including its tip end 4, with exposure of the aforementioned interstice 22', between which body and the shaping device 6 the interstice 22' is present as a return flow channel.

Figure 22:
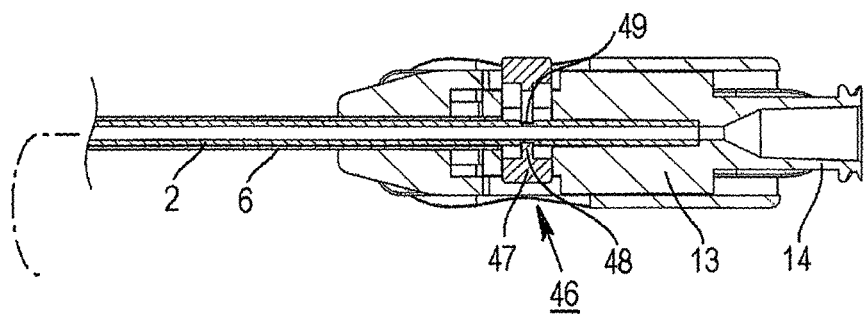
FIG. 22 shows, in a sectional view, not to scale, a proximal contact part of the medical device according to the invention, in which part the first hollow body and the shaping device are accommodated, which have the distal end region of the medical device shown in FIG. 17 to 20.
Figure 23:
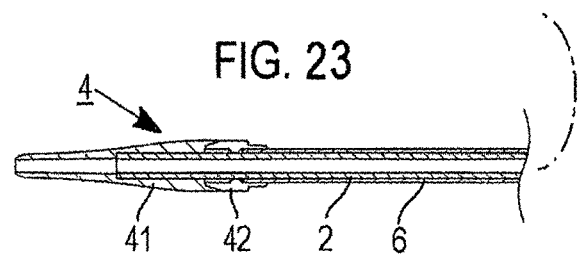
FIG. 23 shows, in a sectional view, not to scale, the distal end region of the first hollow body and of the shaping device according to FIG. 22, in connection with a tip part.

In FIG. 22, a contact part 13 having the first hollow body 2 and the shaping device 6 is shown in a sectional view, not to scale, provided for use in an accommodation part (12 in FIG. 1 to 3) at the proximal end of the medical device according to FIG. 1. The hollow body 2 and the shaping device 6, as indicated with the dot-dash line, are connected with the tip part 4 shown in FIG. 23, which comprises the tip part 41 and the transition part 42. The second hollow body 3 is not shown in FIGS. 22 and 23. This second hollow body 3 is affixed to an accommodation part 12, as shown, for example, in FIG. 12, which has been explained above.

In the contact part 13, the first hollow body 2 is releasably held in place at the proximal device end by a locking mechanism 46. This locking mechanism 46 comprises a slide 47 that can be moved transverse to the longitudinal device direction and introduced into or moved out of a circumferential groove 49 of the first hollow body 2 that runs transverse to the longitudinal device direction with a locking projection 48. In the introduced state, the locking mechanism 46 blocks the first hollow body 2 from being pulled out of the contact part 13; in the moved-out state, the locking mechanism 46 permits the first hollow body 2 to be pulled out of the contact part 13, instead. Together with this pulling out, the tip part 4 is then also pulled away from the distal device end, so that ultimately, only the second hollow body 3 and the shaping device 6 remain there, as shown in FIG. 21.

Figure 24:
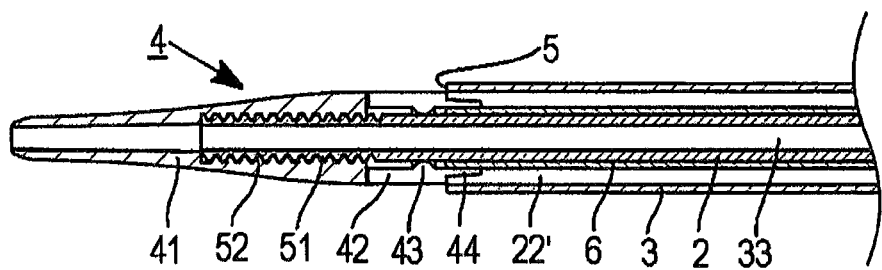
FIG. 24 shows, in a sectional view, not to scale, a distal end region that is modified as compared with the distal end region of the medical device according to the invention shown in FIG. 17, in which the tip part and the first hollow body are connected with one another by a releasable connection device, wherein the shaping device is situated in a first position or adjustment position.
Figure 25:
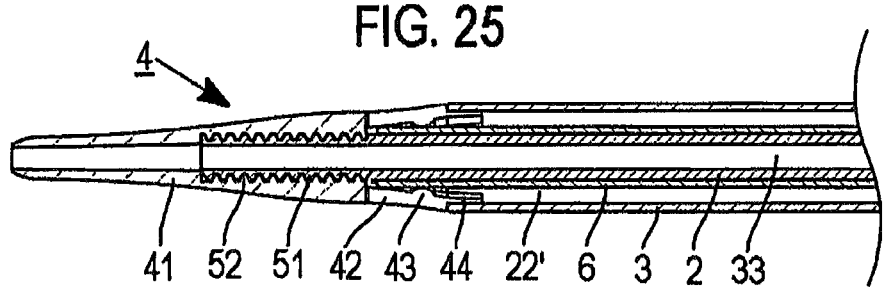
FIG. 25 shows the modified distal end region shown in FIG. 24, wherein the shaping device is situated in a second position or adjustment position different from the first position.
Figure 26:
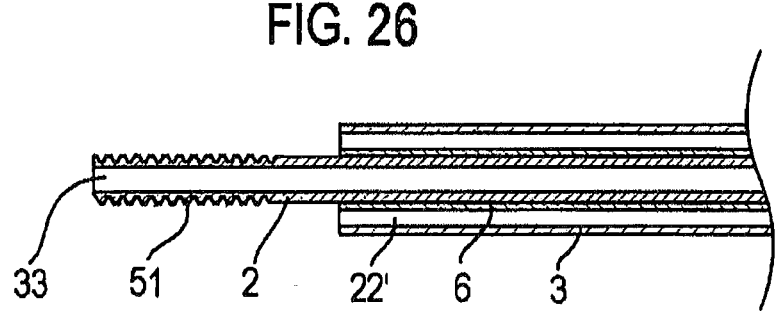
FIG. 26 shows, in a sectional view, not to scale, the distal end region of the medical device shown in FIGS. 24 and 25, after reconfiguration of the device in question to form a flushing device according to the present invention.

In FIG. 24 to 26, yet a further variant of the distal end region of the medical device according to FIG. 1 to 3 is shown, where the device in question, with this distal end region, can also be reconfigured, relatively easily, to form a flushing device according to a third embodiment, as is evident from FIG. 26.

Figure 17:
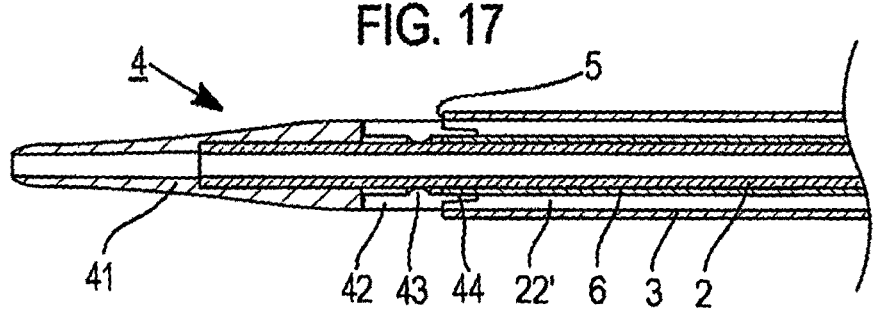
FIG. 17 shows, in a sectional view, not to scale, the distal end region of the medical device according to the invention in a configuration comprising the tip part and the shaping device, in such a manner that is suitable for forming a flushing device according to the present invention, wherein the shaping device is situated in a first adjustment position.
Figure 18:
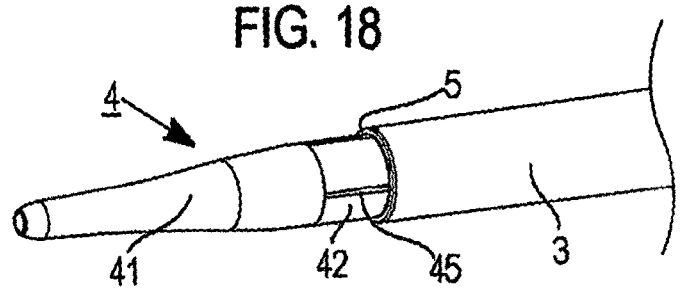
FIG. 18 shows the distal end region of the medical device shown in FIG. 17 in a perspective representation, not to scale.

FIGS. 24 and 25, in sectional views, not to scale, show a distal end region that has been modified as compared with the distal end region shown in FIGS. 17 and 19 of the medical device according to FIG. 1 to 3. In the two FIGS. 24 and 25, elements that agree with elements shown in FIGS. 17 and 19 are referred to with the same reference symbols as there; the shaping device 6 is situated, analogous to FIGS. 17 and 20, in two different positions, a first position in FIG. 24, in which the transition region 5 is formed between the outer second hollow body 3 and the transition part 42, and a second position, different from the first position, in FIG. 25, in which the transition region 5 is made transition-free, at least to a great extent.

The distal end region shown in FIGS. 24 and 25 differs from the distal end region shown in FIGS. 17 and 19 solely in that the tip part 41 and the inner first hollow body 2 are connected with one another by a releasable connection device. With regard to the other elements, the same explanations given with regard to FIGS. 17 and 19 apply to the distal end region according to FIGS. 24 and 25.

The releasable connection device mentioned above is formed by a screw connection device here, which comprises a screw connection part 51 on the distal outer circumference of the first hollow body 2 and a nut connection part 52, which is contained in the tip part 4 here. By releasing this screw connection device 51, 52, the tip part 41, together with the transition part 42, can be removed from the first hollow body 2, so that the distal end region then looks as shown in FIG. 26. After removal of the tip part 4 alone, with exposure of the interstice 22' between the second hollow body 3 and the shaping device 6, toward the distal device end, the inner lumen 33 of the first hollow body 2 can be used as a flushing channel for dispensing a flushing fluid into a bodily orifice or cavity of an individual, into which the medical device according to FIG. 1 to 3 has previously been introduced. In this connection, the said interstice 22' between the second hollow body 3 and the shaping device 6 can be used as a return flow channel for flushing fluid exiting from the bodily orifice or cavity in question, which might be carrying solids with it.

It should be pointed out here that the releasable connection device mentioned above can also be implemented in a manner other than as described here, for example by an engagement connection device between the tip part 4 and the first hollow body 2.

Methods for flushing a bodily orifice or cavity, such as the kidney of an individual, by a flushing fluid introduced into the bodily orifice or cavity in question by the shaping device 6 or the first hollow body 2, are also made possible, in each instance, using the second and third variants of the medical device according to the invention described above using FIG. 17 to 23 as well as FIG. 24 to 26. The flushing fluid exiting from this bodily orifice or cavity again, which might be carrying solids with it, is carried away through the interstice 22 or 22', in each instance, between the outside of the shaping device 6 and the inside of the second hollow body 3, if necessary by suction.

The present medical device according to FIG. 17 to 23 as well as according to FIG. 24 to 26 is particularly used after the medical device 1 described using FIG. 1 to 3 has been introduced into the aforementioned bodily orifice or cavity, and either its first hollow body 2 including its tip part 4 has been removed from the shaping device 6, or only the tip part 4 has been removed, with exposure of the interstice 22, 22', in each instance.

Fundamentally, the methods mentioned above, in connection with FIG. 17 to 23 and FIG. 24 to 26, can also be carried out alone, in each instance, for flushing of bodily orifices or cavities, such as kidneys of individuals, without previously having been configured as medical devices 1 according to FIG. 1 to 3. In this way, the medical devices 1' configured according to FIG. 17 to 23 or FIG. 24 to 26 can also innately be used alone, in each instance, in other words without the additional elements 2, 4, and 6 provided in the medical device 1.

In conclusion, the following should still be noted in this regard. Above all in the case of simultaneous dispensing of a flushing fluid into a bodily orifice or cavity of an individual and return of the flushing fluid exiting from the bodily orifice or cavity in question, which might be carrying solids with it, it is at least advantageous, if not actually required, in all of the embodiments of the medical device according to the invention described above, for perfect operation, that the distance between the distal end of the hollow body or hollow body element dispensing the flushing fluid, in each instance, and the entry location of the flushing fluid to be drained again from the bodily orifice or cavity in question, in the return flow channel, is as great as possible. It is practical if this distance amounts to at least one multiple and preferably at least two multiples of the outside dimension or the outside diameter of the second hollow body 3.

Figure 27:
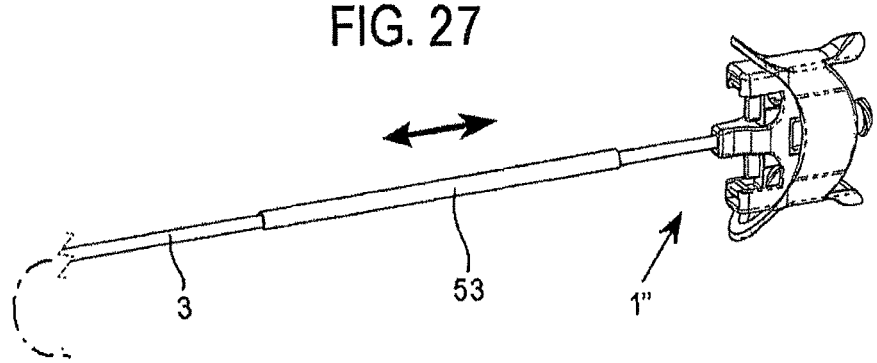
FIG. 27 shows, in a perspective representation, not to scale, the exemplary embodiment of a medical device according to the invention shown in FIG. 1, in which a hollow reinforcement body has been applied to the second hollow body.
Figure 28:
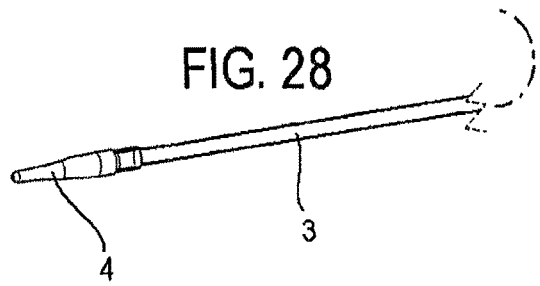
FIG. 28 shows, in a sectional view, not to scale, the distal end region of the second hollow body in connection with a tip part.

In FIGS. 27 and 28, a modification of the exemplary embodiment according to the invention shown in FIG. 1, referred to as 1", is shown in a perspective representation, in a size not to scale, pulled apart and connected with a dot-dash line. According to FIG. 27, a hollow reinforcement body 53, which can be a tube or hose composed of a biocompatible material, for example, is applied to the second hollow body 3. By this hollow reinforcement body 53, a rigidity that is increased as compared with the rigidity of the two hollow bodies can be imparted to the medical device 1" in the region of its two hollow bodies, of which only the hollow body 3 can be seen in FIGS. 27 and 28; such rigidity can occasionally be desired when using the medical apparatus 1" in question. Depending on the application case, hollow reinforcement bodies 53 having different rigidity values can be used, in this connection.

Figure 29:
FIG. 29 shows, in a magnified sectional view, a possible cross-sectional shape of the hollow reinforcement body.
Figure 30:
FIG. 30 shows, in a magnified sectional view, an alternative cross-sectional shape of the hollow reinforcement body.

The hollow reinforcement body 53 can have different shapes, in terms of its cross-section, as they are illustrated, for example, in the two sectional view according to FIG. 29 and FIG. 30.

In the case of the round, closed hollow cross-sectional shape shown in FIG. 29, the hollow reinforcement body referred to as 53r can be pushed or can have been pushed onto the second hollow body 3 of the medical device 1" from the distal end of the device. In the case of the open, C-shaped cross-sectional shape shown in FIG. 30, the hollow reinforcement body referred to as 53c can also be either pushed or clamped onto the second hollow body 3 of the medical device 1.

In this connection, the hollow reinforcement body 53 or 53r or 53c, in each instance, can be applied to the hollow body 3 either as a single element, or it can be applied to the body in a plurality, for example applied doubly or triply, one after the other. In this connection, the individual hollow reinforcement bodies applied to the hollow body one after the other can have the same or different rigidity values. Furthermore, hollow reinforcement bodies can also be applied to the hollow body one on top of the other, either by pushing them on or clamping them on, in the case of the cross-sectional shape shown in FIG. 30.

REFERENCE SYMBOL LIST 1, 1" medical device or dilator
1' medical device or flushing device
2 first hollow body, dilator tube
3 second hollow body, outer tube
4 tip part
5 step-shaped transition
6, 6a, 6b shaping part
7, 7a pressing part
8 accommodation space
9 step-free transition
10 depression part
11 slide mechanism
12 accommodation part
13 contact part
14 connection part
15 inner part
16 outer part
17 sliding part
18 engagement projections
19 engagement projection accommodations
20 stop
21 third hollow body
22, 22' interstice
23, 24 activation element
25, 26 engagement element
27, 28 accommodation
29 continuous lumen
32 lumen, flushing channel
33 lumen, flushing channel
41 tip part
42 transition part
43 nub region
44 contact part(s)
45 slit(s)
46 locking mechanism
47 slide
48 locking projection
49 circumferential groove
51 screw connection part
52 nut connection part
53, 53r, 53c hollow reinforcement body

The invention claimed is:

1. Medical device (1) for introduction into a bodily orifice or cavity of an individual, having a proximal end and a distal end and a first elongated hollow body (2) with a proximal end and a distal end and a second elongated hollow body (3) with a proximal end and a distal end, wherein the first hollow body is accommodated in the second hollow body (3)
wherein the distal end of the first hollow body (2) is configured as a tip part (4) or has a tip part (4) which has a proximal end and a distal end, wherein the distal end of the tip part (4) is intended for the introduction into a bodily orifice or cavity of an individual, wherein the proximal end of the tip part (4) extends to the distal end of the second hollow body (3), forming a step-shaped transition (5), wherein said step-shaped transition extends in the radial direction of the tip part (4) and the second hollow body (3),
wherein a shaping device (6, 7; 6, 10) that can be displaced in its longitudinal direction is accommodated between the tip part (4) and the second hollow body (3),
and wherein the shaping device (6, 7; 6, 10) has such a shape that by its displacement in the longitudinal direction of the medical device in the region of the step-shaped transition (5), at least one of the proximal end of the tip part (4) and the distal end of the second hollow body have a change in diameter in a radial direction such that both the distal end of the second hollow body and the proximal end of the tip part have equal outside diameters, and the step-shaped transition (5), is transformed, at least to a great extent, into a step-free transition (9).

2. Medical device (1) according to claim 1, wherein the second hollow body has a greater outside dimension than an outside dimension of the tip part and wherein the shaping device (6, 7; 6, 10) contains a shaping part (6) that has a pressing part (7) on its outside, such that by longitudinally moving said pressing part in the region of the step-shaped transition (5) between the tip part (4) and the second hollow body (3), the tip part (4) can be expanded in the radial direction with its outer dimension toward the greater outside dimension of the second hollow body (3).

3. Medical device (1) according to claim 1 wherein the shaping device (6, 7; 6, 10) has a shaping part (6) that has a depression part (10) on its outside, in its region to be moved toward the step-shaped transition (5) between the tip part (4) and the second hollow body (3), by which depression part the second hollow body (3), which has the greater outside dimension in the radial direction, in the adjacent region between the tip part (4) and the second hollow body (3), can be lowered all the way to the tip part (4), which has the smaller outside dimension in the radial direction.

4. Medical device (1) according to claim 1, wherein a slide mechanism (11) is connected with at least the one of the two hollow bodies (2, 3) and the shaping device (6, 7; 6, 10) in such a way that by the activation of said mechanism the shaping device (6, 7; 6, 10) can be displaced relative to at least the one of the two hollow bodies (2, 3) in the longitudinal direction of the hollow body.

5. Medical device (1) according to claim 4, wherein the slide mechanism (11) consists of an accommodation part (12) connected with the one of the hollow bodies (2, 3) and a contact part (13) connected with the shaping device (6, 7; 6, 10), wherein said contact part can be accommodated by the accommodation part (12) and can be displaced relative to the latter in the longitudinal direction of the hollow bodies.

6. Medical device (1) according to claim 5, wherein the slide mechanism (11) has a locking device (18, 19) that allows displacement of the shaping device (6, 7; 6, 10) relative to at least one of the hollow bodies (2, 3), only after or during the course of locking of the contact part (13) on or in the accommodation part (12).

7. Medical device (1) according to claim 1, wherein the device is configured as a medical dilator (1), which serves for introduction into a bodily orifice or cavity of an individual, wherein the first hollow body is formed by a dilator tube (2) configured as the tip part (4) or connected with the tip part (4), and which is accommodated by an outer tube (3) formed by the second hollow body (3), and wherein the shaping device (6, 7; 6, 10), which can be displaced in the longitudinal direction, is accommodated between the outer tube and the dilator tube.

8. The medical device according to claim 1, wherein displacement of the shaping device in the longitudinal direction of the medical device in the region of the step-shaped transition (5) expands the proximal end of the tip part in the radial direction, such that the step-shaped transition (5) toward the second hollow body (3) is transformed, at least to a great extent, in a step-free transition.

* * * * *